US00PP32550P3

(12) United States Plant Patent
Eveleens et al.

(10) Patent No.: US PP32,550 P3
(45) Date of Patent: Dec. 1, 2020

(54) ***HYDRANGEA* PLANT NAMED 'HOKOMACHOKO'**

(50) Latin Name: *Hydrangea macrophylla*
Varietal Denomination: Hokomachoko

(71) Applicants: Horteve Breeding BV, Aalsmeer (NL); Kolster Holding BV, Boskoop (NL)

(72) Inventors: Cornelis Pieter Eveleens, Aalsmeer (NL); Peter Rudolf Kolster, Boskoop (NL)

(73) Assignees: HORTEVE BREEDING BV, Aalsmeer (NL), part interest; KOLSTER HOLDING BV, Boskoop (NL), part interest ( * ) Notice: Subject to any disclaimer, the term of this patent is extended or adjusted under 35 U.S.C. 154(b) by 0 days.

(21) Appl. No.: 16/602,056

(22) Filed: Jul. 25, 2019

(65) Prior Publication Data

US 2020/0170161 P1 May 28, 2020

(30) Foreign Application Priority Data

Nov. 27, 2018 (QZ) ..... PBR 2018/3091

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48
See application file for complete search history.

*Primary Examiner* — Anne Marie Grunberg
(74) *Attorney, Agent, or Firm* — Penny J. Aguirre

(57) ABSTRACT

A new cultivar of *Hydrangea macrophylla* plant named 'Hokomachoko' that is characterized by its inflorescences that are dark red in color and flattened in shape, its vigorous growth habit, its suitability as a cut flower use and as a potted plant, and its upright growing habit.

2 Drawing Sheets

Botanical classification: *Hydrangea macrophylla.*
Varietal denomination: 'Hokomachoko'.

CROSS REFERENCE TO RELATED APPLICATIONS

This application is related to U.S. Plant Patents for a plant derived from the same breeding program that are entitled *Hydrangea* Plant Named 'Hortmagibo' (U.S. Pat. No. 30,267), *Hydrangea* Plant Named 'Hortmalegretto' (U.S. Plant Pat. No. 30,045), and *Hydrangea* Plant Named 'Kolmaru' (U.S. Plant Pat. No. 25,104).

BACKGROUND OF THE INVENTION

The present invention relates to a new and distinct cultivar of *Hydrangea macrophylla* and will be referred to hereafter by its cultivar name, 'Hokomachoko'. 'Hokomachoko' represents a new bigleaf *Hydrangea*, a perennial shrub grown for use as a potted plant and cut flower.

'Hokomachoko' derived from an ongoing controlled breeding program directed by the Inventors. An objective of the breeding program included developing a new cultivar of *Hydrangea* with red color flowers, a floriferous blooming habit and sturdy flower sepals.

'Hokomachoko' arose from a controlled cross made by the Inventor in Boskoop, The Netherlands in June of 2012 between an unnamed and unpatented proprietary plant in the Inventor's breeding program (reference no. 09-025-05) as the female parent and *Hydrangea* 'Kolmaru' as the male parent. 'Hokomachoko' was selected as a single unique plant from amongst the resulting seedlings in June of 2014.

Asexual propagation of the new cultivar was first accomplished by stem cuttings by one of the Inventors in August of 2014 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomachoko' as a unique cultivar of *Hydrangea macrophylla.*

1. 'Hokomachoko' exhibits inflorescences that are dark red in color and flattened in shape.
2. 'Hokomachoko' exhibits a vigorous growth habit.
3. 'Hokomachoko' exhibits suitability as a cut flower use and as a potted plant.
4. 'Hokomachoko' exhibits an upright growing habit.

The female parent of 'Hokomachoko' differs from 'Hokomachoko' in having flowers that are green-pink in color, sepals that are softer in texture and shorter stems. The male parent of 'Hokomachoko' differs from 'Hokomachoko' in having inflorescences that are lighter red in color and globular in shape and sepals that are softer in texture. 'Hokomachoko' can be most closely compared to the *Hydrangea macrophylla* cultivars 'Hortmagibo' and 'Hortmalegretto'. 'Hortmagibo' and 'Hortmalegretto' are both similar to 'Hokomachoko' in having red color inflorescences and upright growing habits. 'Hortmagibo' and 'Hortmalegretto' both differ from 'Hokomachoko' in having a globular shaped inflorescences and inflorescences that are lighter red in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to a website listing by Plants Nouveau.

BRIEF DESCRIPTION OF THE DRAWINGS

The accompanying colored photographs illustrate the overall appearance and distinct characteristics of the new *Hydrangea*. The photographs were taken of a three-year-old plant of 'Hokomachoko' as grown in a greenhouse in a 27-cm container in Boskoop, The Netherlands.

The photograph in FIG. 1 provides a side view of the plant habit of 'Hokomachoko' in bloom.

Figure 1:
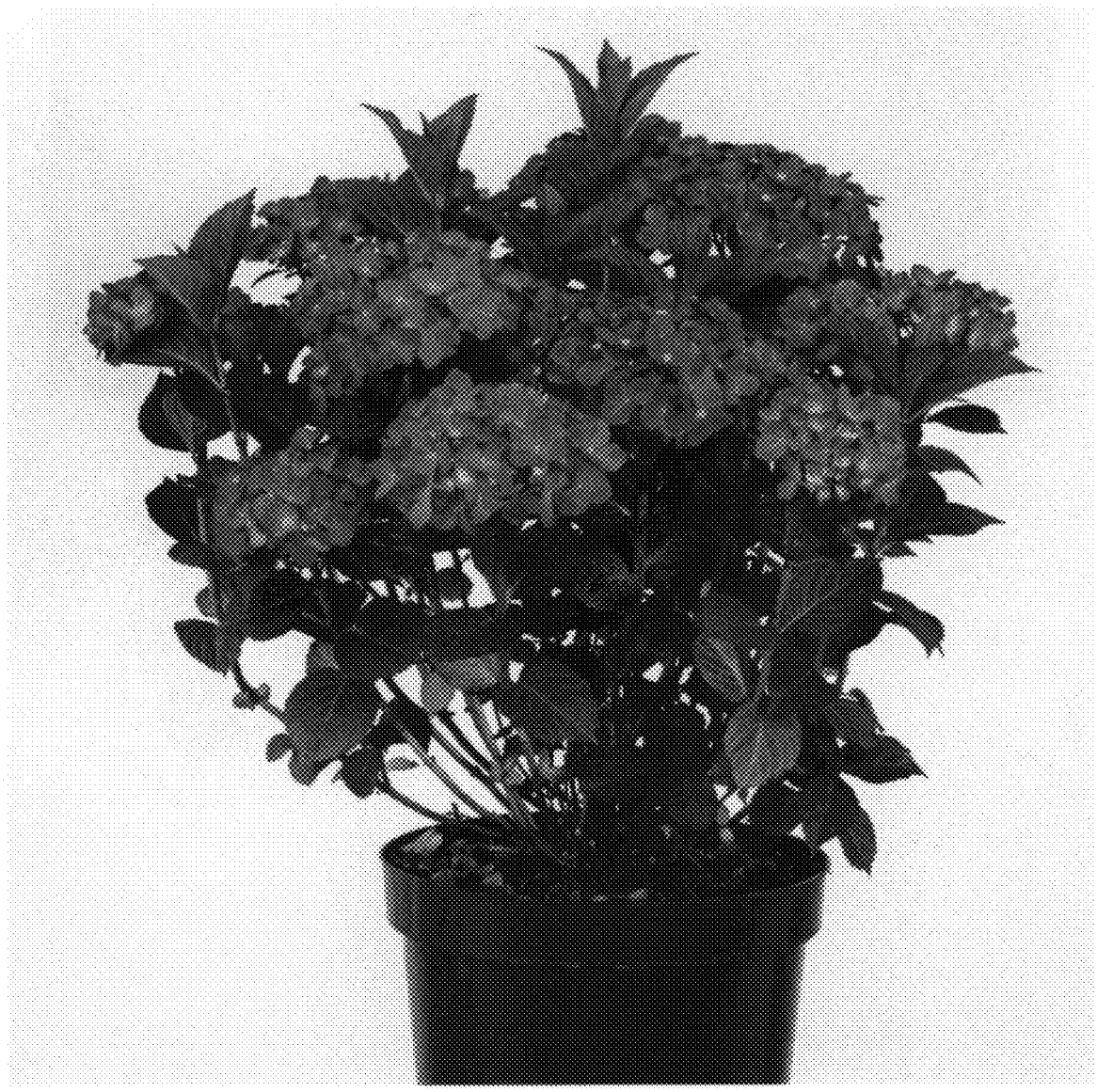
Figure 2:
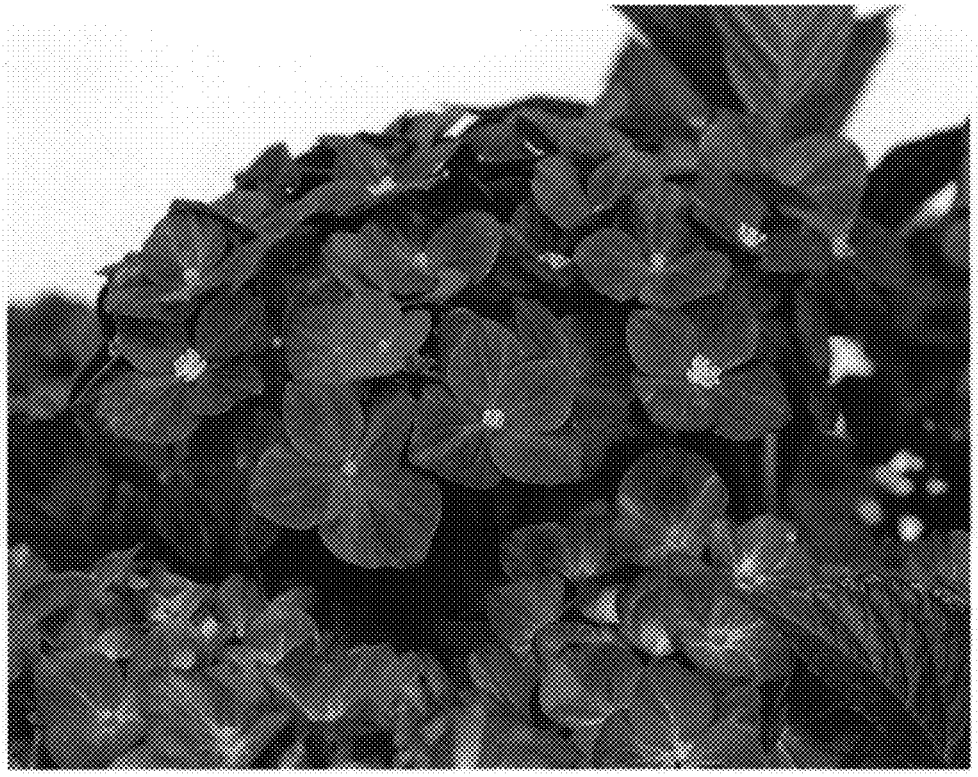

The photograph in FIG. 2 provides a close-up view of a fully open inflorescence of 'Hokomachoko'.

Figure 3:
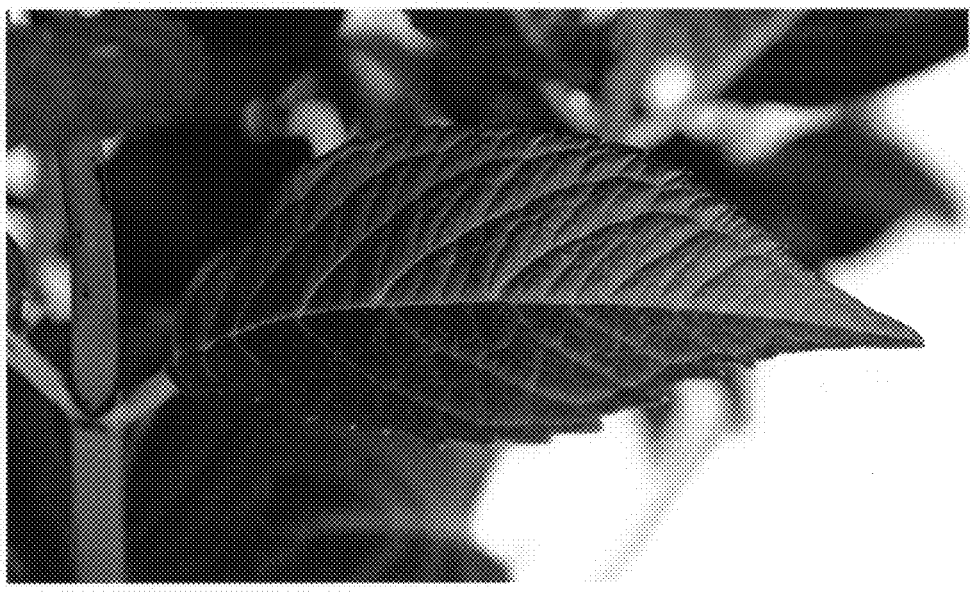

The photograph in FIG. 3 provides a close-up view of a leaf of 'Hokomachoko'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of three-year-old plants of 'Hokomachoko' as grown in a greenhouse in 27-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*. —Late spring to late summer with flowers showy at least for 2 months in the Netherlands.

*Plant type*. —Deciduous shrub, mophead type *Hydrangea*.

*Plant habit*.—Spreading, upright.

*Height and spread*.—An average of 50 cm in in height and 66.5 cm in spread as grown in a 27-cm container, reaches 1 m in height and spread as a 3-year-old plant in the landscape.

*Hardiness*.—At least in U.S.D.A. Zones 5 to 9.

*Diseases and pests*.—No susceptibility and resistance to diseases or pests has been observed.

*Root description*.—Fine and fibrous, 161C in color.

*Propagation*.—Stem cuttings.

*Root development*.—An average of 6 weeks for root initiation with a young rooted plant produced in an average of 18 weeks.

*Growth rate and vigor*.—Vigorous.

Stem description:

*Stem shape*.—Rounded.

*Stem strength*.—Strong.

*Stem color*.—Young; 144A, mature; 144A, internodes tinged with N186C, old bark; 199C to 199D and N199B.

*Stem size*.—An average of 29.4 cm in length (excluding inflorescence) and 5.5 mm in diameter.

*Stem surface*.—Glabrous, sparsely lenticellate, lenticels; an average of 3 mm in length and 1.25 mm in diameter, N186C in color.

*Stem aspect*.—Average angle of vertical to 30°.

*Internode length*.—An average of 5.7 cm.

*Branching*.—Freely branching with an average of 39 lateral branches.

Foliage description:

*Leaf shape*.—Ovate to broad ovate.

*Leaf arrangement*.—Opposite.

*Leaf division*.—Simple.

*Leaf base*.—Short attenuate to obtuse.

*Leaf apex*.—Apiculate.

*Leaf margins*.—Coarsely serrate.

*Leaf venation*.—Pinnate, color; color upper surface 144A, lower surface 144C.

*Leaf size*.—An average of 8.3 cm in length and 5.3 cm in width.

*Leaf attachment*.—Petiolate.

*Leaf number*.—An average of 14 per lateral stem.

*Leaf surface*.—Both surfaces; smooth and moderately rugose.

*Leaf color*.—Young foliage; upper surface between 137A and 143A, outer edges 200A, lower surface 146B, outer edge 200A, mature foliage; upper surface between NN137A and 147A, outer edge tinged 200B to 200C, lower surface 147A, outer edge tinged 200B to 200C.

*Petioles*.—An average of 9.5 mm in length and 3 mm in diameter, upper surface color N144A, lower surface color 144B to 144C and N186C, both surfaces are smooth and slightly glossy.

Inflorescence description:

*Inflorescence type*.—Terminal panicle, flattened mophead comprised of sterile flowers above fertile flowers.

*Lastingness of inflorescence*.—Sterile flowers; persistent for an average of 6 weeks, fertile flowers; self-cleaning, an average of 5 days.

*Lastingness of as a cut flower*.—An average of 2 weeks.

*Inflorescence number*.—One per lateral stem.

*Inflorescence size*.—An average of 9.7 cm in height and 17.3 cm in diameter.

*Flower number*.—An average of 150 sterile flowers and 55 fertile flowers per panicle.

*Flower fragrance*.—None.

*Flower aspect*.—Upright to outward.

*Flower size*.—Sterile flowers; an average of 3.5 cm in diameter and 7 mm in depth, fertile flowers; an average of 7 mm in diameter and 4 mm in depth.

*Flower type*.—Rotate.

*Flower buds*.—Sterile flowers; an average of 1 cm in length and 1.3 cm in diameter, cup shaped, 145C, tip 48C in color, fertile flowers; an average of 4 mm in length and diameter, spherical in shape, color; 48C, 137C to 137D at base.

*Peduncles*.—Strong, flattened oval in shape, an average of 2 cm in length and 2 mm in width on primary peduncles and secondary peduncles 1.2 cm in length and 2 mm in width, and blend of 145C and 180D in color in color, surface matte and sparsely to moderately covered with thin pubescence an average of 0.2 mm in length and too small to measure color.

*Pedicels*.—Sterile flowers; held primarily at an average angle of 40° to upright, an average of 1.9 cm in length and 1 mm in diameter, moderately strong strength, 180D in color, surface matte and sparsely to moderately covered with thin pubescence an average of 0.2 mm in length and too small to measure color, fertile flowers; held at an average angle of 25° from vertical, an average of 3.5 mm in length and 1 mm in diameter, moderate strength, 145C in color, matte surface and very sparsely covered with thin pubescent hairs an average of 0.2 mm in length and too small to measure color.

*Petals*.—Sterile flowers; an average of 4, rotate, cruciform in arrangement, acute apex, cuneate base, entire margins, ovate to moderately to strongly concave in shape, average of 4 mm in length and 2.5 mm in width, both surfaces; glabrous and matte, color; when opening and fully open upper surface 70B, changing to NN155D at the base, when opening and fully open lower surface 63B, color not fading, but dropped when mature, fertile flowers; an average of 4 to 5, rotate in arrangement, ovate and concave in shape, entire margin, acute apex, cuneate base, an average of 4 mm in length and 2 mm in width, upper and lower surface glabrous and matte, color; upper surface when opening and fully open 64D, lower surface when opening and fully open 69D, tinged 146D, base changing to 63C.

*Sepals*.—Sterile flowers; 3 to 4, rotate, rotate, bluntly acute to near obtuse apex, broadly cuneate base, entire margins, broad ovate to reniform in shape, an average of 1.9 cm in length and 2.1 cm in width, upper surface glabrous and matte, lower surface glabrous and very slightly glossy, color; when opening upper surface 60A, changing to 61C at the base, when opening lower surface 68B, very slightly tinged 148C, when fully open upper surface 60A to 60B, irregularly blotched with 147A and 197A, when fully open lower surface N148B to N148C, veined 63B to 63C, upper surface fading to 146A to 147A and strongly tinged 187C, lower surface fading to 147C, 61D at the base, fertile flowers; an average of 5 to 6, ovate to elliptic in shape, entire margin, acute apex, 3 mm in length, 1.5 cm width, and cuneate base, both surfaces are glabrous and matte, color; upper surface when opening and fully open 137C to 137D, lower surface when opening and fully open 141A.

*Ph sensitivity*.—The inflorescence color will experience a blueing effect when grown with added aluminum sulfate and a soil pH of <6.5, plants have not been grown under these conditions except for trial purposes, sepals of the sterile flowers at maturity on both surfaces is a blend of 91A and 92B, the bueing coloration of the fertile flowers has not been recorded.

Reproductive organs:

*Gynoecium*.—Sterile flowers; 2 pistils, an average of 1 mm in length, stigma; club-shaped and NN155C in color, style; 0.5 mm in length, 58C to 58D in color, ovary is 62C in color, fertile flowers; an average of 3 pistils, an average of 1.75 mm in length, stigma; club-shaped and NN155C in color, style; 1 mm in length and 65D in color, ovary is 150D in color.

*Androecium*.—Sterile flowers; an average of 8 stamens, filaments; an average of 2.75 mm in length and N155B in color, anthers; broad oblong in shape, an average of 0.75 mm in length and 155D in color, pollen; low in quantity, 155D in color, fertile flowers; an average of 10 stamens, filaments; an average of 3 mm in length and NN155D in color, anthers; broad oblong in shape, an average of 0.75 mm in length and 155D in color, pollen; low in quantity and 155D in color.

*Fruit and seed*.—None observed to date.

It is claimed:

1. A new and distinct cultivar of *Hydrangea* plant named 'Hokomachoko' substantially as herein illustrated and described.

* * * * *